United States Patent [19]

Mease et al.

[11] Patent Number: 5,334,729

[45] Date of Patent: Aug. 2, 1994

[54] STABLE RADIOMETAL ANTIBODY IMMUNOCONJUGATES

[75] Inventors: Ronnie C. Mease, Coram; Suresh C. Srivastava, Setauket, both of N.Y.; Jean-François Gestin, Oudon, France

[73] Assignee: Associated Universities, Inc., Washington, D.C.

[21] Appl. No.: 787,244

[22] Filed: Nov. 4, 1991

Related U.S. Application Data

[60] Division of Ser. No. 679,258, Apr. 2, 1991, Pat. No. 5,089,663, which is a continuation-in-part of Ser. No. 872,905, Jun. 29, 1989, Pat. No. 5,021,571.

[51] Int. Cl.$^5$ .................. C07D 207/46; C07C 281/02
[52] U.S. Cl. ..................................... 548/546; 562/507; 564/462
[58] Field of Search ........................ 548/546; 562/507; 564/462

[56] References Cited

U.S. PATENT DOCUMENTS 4,352,751 10/1982 Wieder et al. ...................... 260/112
4,707,440 11/1987 Stavrianopoulos ...................... 435/6

FOREIGN PATENT DOCUMENTS 0279307 8/1988 European Pat. Off. .
3324236A1 12/1980 Fed. Rep. of Germany .

OTHER PUBLICATIONS

Takeshita, et al., *JAOCS*, 59, No. 2 (Feb. 1982).

*Primary Examiner*—David B. Springer
*Attorney, Agent, or Firm*—Margaret C. Bogosian

[57] ABSTRACT

The present invention relates to new rigid chelating structures, to methods for preparing these materials, and to their use in preparing radiometal labeled immunoconjugates. These new chelates include cyclohexyl EDTA monohydride, the trans forms of cyclohexyl DTPA and TTHA, and derivatives of these cyclohexyl polyaminocarboxylate materials.

4 Claims, No Drawings

STABLE RADIOMETAL ANTIBODY IMMUNOCONJUGATES

This invention was made with Government support under contract number DE-AC02-76CH00016, between the U.S. Department of Energy and Associated Universities, Inc. The Government has certain rights in the invention.

RELATED APPLICATION

The instant application is a divisional application of co-pending application Ser. No. 679,258 filed Apr. 2, 1991, now U.S. Pat. No.5,089,663 issued Feb. 18, 1992, which in turn is a continuation-in-part of application Ser. No. 872,905 filed Jun. 29, 1989, now U.S. Pat. No. 5,021,571 issued Jun. 4, 1991.

BACKGROUND OF THE INVENTION

Radiometals offer distinct advantages over iodine when used to label monoclonal antibodies. Radiometals that bind to antibodies by chelation help avoid the deleterious effects of oxidation experienced in common iodination reactions. Labeling with metals also overcomes the problems of in-vivo deiodination by tumor and normal tissues, particularly when using rapidly internalized antibodies. Radiometals also provide a wealth of choices of half-life and emissions for various applications (diagnosis or therapy).

Radiometals can generally be attached to antibodies by the use of a "bifunctional chelate" which is first covalently attached to the antibody to form an antibody-chelate conjugate which then binds the radiometal. The most commonly used chelate is DTPA and it is generally conjugated to antibodies via bicyclic DTPA anhydride, which forms a covalent amide bond between an antibody amine and one of the carboxylic acid groups of DTPA [Hnatowich, et al., Science, 220, 613 (1983)]- This method, however, has drawbacks. The use of this procedure yields high liver retention and slow body clearance [Goodwin, J. Nucl. Med., 28, 1358 (1987)], as well as a substantial amount of crosslinked antibody (two antibodies linked together by a DTPA bridge). This crosslinking increases liver retention and decreases tumor uptake.

The use of liposome-encapsulated $^{111}$In-$^{14}$C-DTPA showed that the $^{14}$C-DTPA is cleared through the kidney into the urine while the $^{111}$In remains in the liver [Mathias, et al., J. Nucl. Med., 28, 657 (1987)]. This suggests that the retention of indium is due to its transchelation in the liver following its detachment from DTPA, indicating that chelates which form stronger complexes with $^{111}$In will be necessary in order for the $^{111}$In-chelate complex to survive liver catabolism of the antibody-chelate conjugate and be excreted intact through the kidney into the urine. The introduction of benzyl groups onto the backbone of EDTA and DTPA has been shown to increase the serum stability of $^{111}$In-EDTA and -DTPA chelates and antibody conjugates [see, for example, Cole, et al., Nucl. Med. Biol., 13,363 (1986)].

In spite of these improvements, benzyl EDTA and benzyl DTPA are not the optimal chelates for all radiometals. For example, copper-67 1-(p-isothiocyanatobenzyl)EDTA labeled antibodies are very unstable in serum and require the use of macrocyclic ligands [Cole, et al., J. Nucl. Med., 28, 83 (1987)] or porphyrins [Mercer-Smith, et al., Los Alamos National Laboratory Report LA-10709-PR, 58 (1986)] to form complexes that are stable in serum.

As discussed above, one strategy followed to overcome the problems caused by liver catabolism is to use chelates that form more stable radiometal complexes on the immunoconjugate so that the radiometal chelate can survive the liver metabolism of the antibody intact. A second approach to this problem is to place a metabolizable linking group between the antibody and radiometal chelate so that the linker is rapidly cleaved, thereby reducing the time the chelate resides in the liver and the opportunity for transchelation with hepatic proteins. Several groups have been investigating this approach. Faster whole body clearance and higher tumor/tissue ratios have been obtained with linkers containing a disulfide or an ester between the antibody and DTPA-p-(aminoethyl) anilide [Paik, et al., J. Nucl. Med., 28, 572 (1987)]. Linking groups containing either a disulfide, ester, thioether, thiourea, or peptide group have been placed between the antibody and the para-amino group of p-aminobenzyl EDTA. While the disulfide clearance is promising it would appear that the disulfide clearance occurs in the circulation and may be too rapid for use with antibodies [see Deshpande, et al., Nucl. Med. Biol., 16, 587 (1989)].

One object of the present invention is the preparation of ligands that will form radiometal chelates that are capable of surviving in-vivo. This is accomplished by combining the rigidity of the ligand with the general utility of polyaminocarboxylates such as EDTA and DTPA, for example by the substitution of a rigid molecule such as trans-1,2-diaminocyclohexane for an ethylene diamine portion of a polyaminocarboxylate. The rigidity of the cyclohexane ring fixes two of the nitrogens into a position where they can readily complex radiometals. The semi-rigid chelate cyclohexyl EDTA is known and has been used in the preparation of copper complexes [Robinson, Prog. Nucl. Med., 4, 80 (1978)]. The present invention relates to new semi-rigid chelates that bind the radiometal, can be conjugated to monoclonal antibodies, and overcome the stability problems of the prior art materials.

DETAILED DESCRIPTION OF THE INVENTION

This invention relates to the preparation of new forms and derivatives of the semi-rigid chelate, cyclohexyl EDTA ("CDTA").

This invention relates to the synthesis of the new monoanhydride form of cyclohexyl EDTA and its separation from its dianhydride. This monofunctionalized semi-rigid chelate can be readily attached to a monoclonal antibody predominantly through lysine groups on the antibody without crosslinking of the antibody. The immunoconjugates formed using this chelating agent produce stable complexes with many radiometals. Many of these complexes are more stable in serum than those formed using non-rigid chelates such as EDTA and DTPA.

This invention also relates to the family of new compounds produced by the derivatization of the monoanhydride of cyclohexyl EDTA depicted by the formula

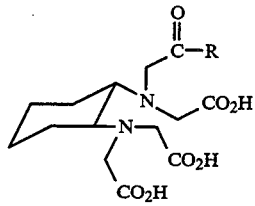

wherein R is:

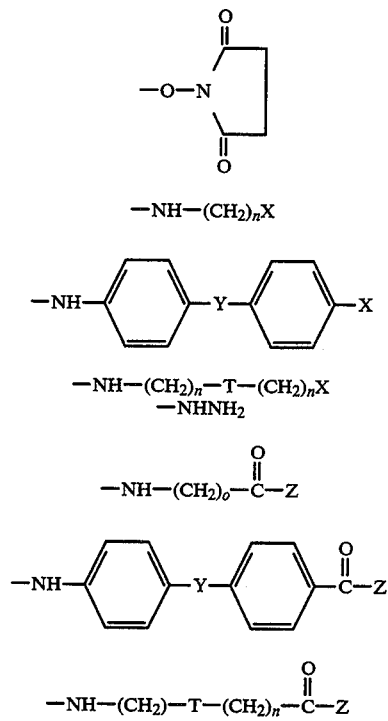

Y is:
—CH$_{12}$—
—O—
—S—
—S—S—

X is:

—NH$_2$

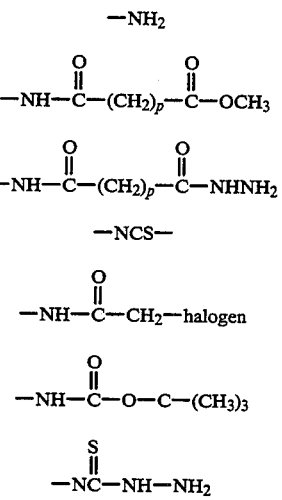

T is:

—O—
—S—
—S—S—

Z is:
-lower alkoxy containing from 1 to 6 carbon atoms
—NHNH$_2$
n is 2 to 6
o is 1 to 6
p is 2 to 4 and
halogen is Cl, Br and I.

Cyclohexyl EDTA monoanhydride (CDTAMA) can be derivatized by converting one and only one of the carboxyl groups to a moiety that is also capable of conjugation to antibodies, such as the N-hydroxysuccinimide ("NHS") ester (the compound of formula I wherein R is

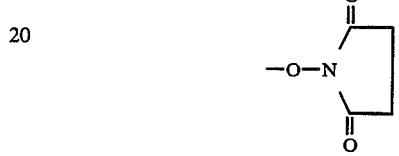

The reaction of hydrazine with CDTAMA will yield the hydrazide (the compound of formula I wherein R is —NHNH$_2$) which will permit its attachment to the carbohydrate region of the antibody after the antibody is treated with sodium periodate. CDTAMA is also a valuable synthetic intermediate to attach one and only one linker or spacer group between the chelate and antibody. These linker or spacer groups may contain groups that can be metabolized by enzymes in non-target organs to speed the clearance of the radiometal-chelate complex from the non-target organ. For example monoprotected amines can be prepared using CDTAMA and the corresponding monoprotected diamine. Acid hydrolysis of the protecting group yields the corresponding amines (the compounds of formula I wherein X is NH$_2$). These amines can be attached to antibodies by a Schiff-base reaction with aldehydes on the carbohydrate region of the antibody. Additionally these amines can be converted to groups that can be attached to lysine groups on the antibody by conversion of the terminal amines to isothiocyanates (the compounds of formula I wherein X is NCS—see Scheme 1 which follows) by reaction with thiophosgene, and to halo-acetamides by reaction with a haloacetyl halide such as bromoacetyl bromide or the N-hydroxysuccinimide ester of α-Bromoacetic acid. These amines can also be used to add other linker and spacer groups to CDTA (Scheme 1 following) by their reaction with linear molecules containing terminal NHS esters and internal functional groups.

Thiosemicarbazides (the compounds of formula I wherein

which can react with the aldehydes of the carbohydrate region of the antibody like hydrazides, can be prepared from the reaction of isothiocyanates with hydrazine. Also amide-esters (the compounds of formula I wherein Z is lower alkoxy) can be prepared using CDTAMA and the corresponding amine-esters. These esters can then be converted to hydrazides by their reaction with hydrazine.

The compounds of formula I wherein X is

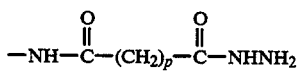

are available from the reaction of hydrazine with esters. These esters are obtained from the reaction of CDTAMA with the corresponding amine-ester. These amine esters can be prepared from the reaction of the monoprotected diamine with an acid chloride ester such as methyl glutaryl chloride.

A further aspect of the present invention relates to the preparation of the trans-cyclohexyl derivatives of DTPA and TTHA which are synthesized as outlined in Reaction Scheme 2 which follows. A synthesis of CDTPA has been reported [Dexter, German Patent 1,155,122 (1963)]. This reaction, however, apparently results in a mixture of cis and trans-diamino products. Since the cis (axial-equatorial) compounds will not bind metals as strongly as the trans (diequatorial) compound, this synthesis is not a useful one for the purposes of the present invention. The products resulting from Reaction Scheme 2 are strictly trans.

In a further aspect of the present invention, CDTPA and CTTHA are converted to the corresponding mono-NHS ester-cyclohexyl chelates, which can be further modified, using the chemical transformations outlined above for CDTAMA.

Modifications of the CDTPA chelate leads to derivatives of the formula

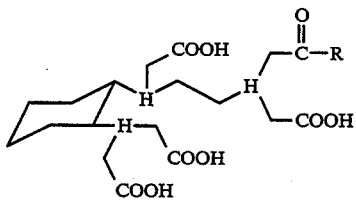

wherein R is as defined above.

Modification of the CTTHA chelate leads to derivatives of the formula

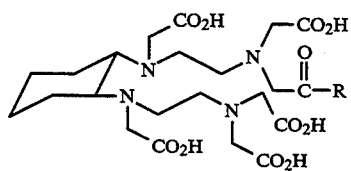

wherein R is as defined above.

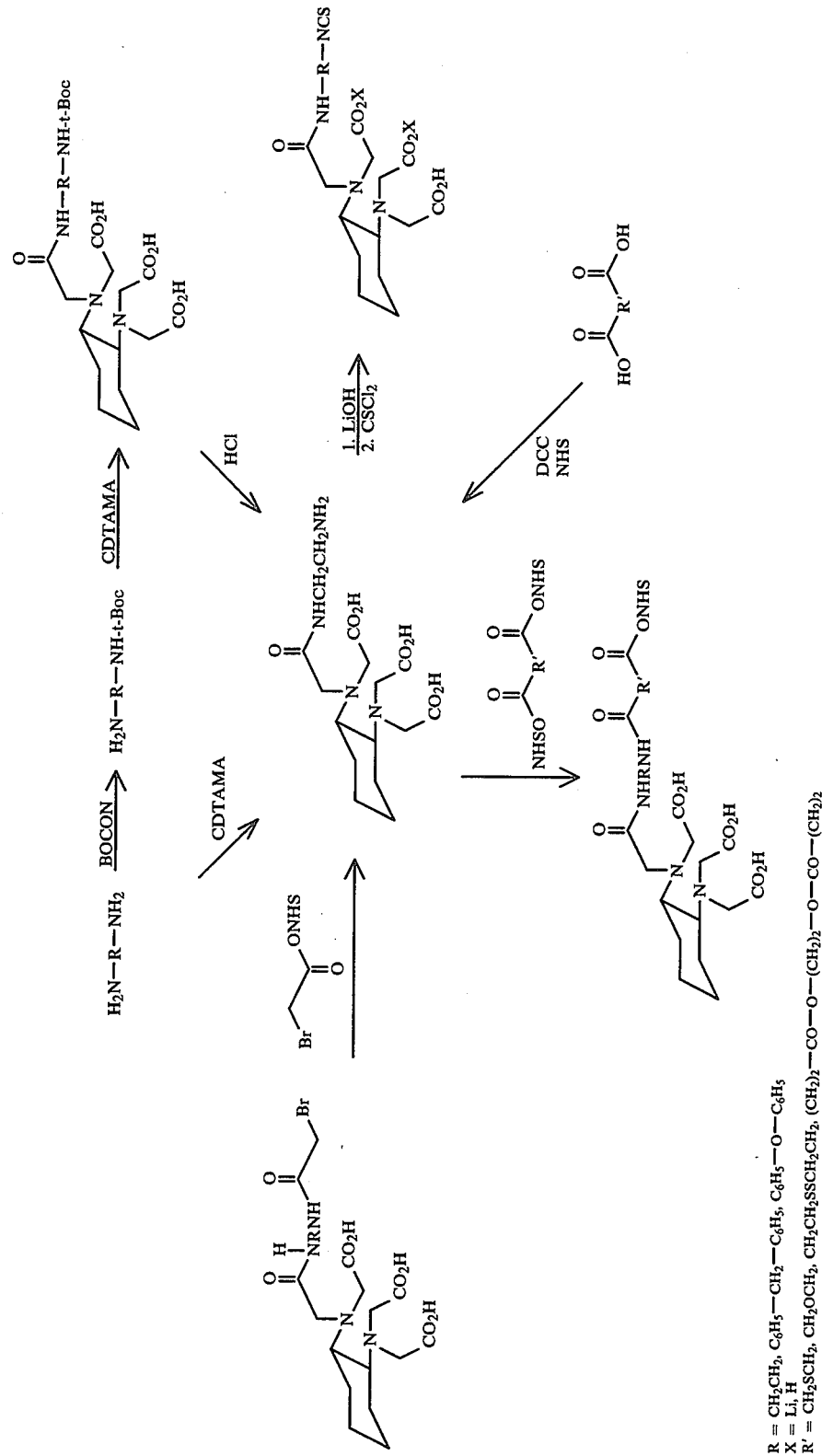

R—CH₂CH₂, C₆H₅—CH₂—C₆H₅, C₆H₅—O—C₆H₅
X=Li, H
R'=CH₂SCH₂, CH₂OCH₂, CH₂CH₂SSCH₂CH₂,
(CH₂)₂—CO—O—(CH₂)₂—O—CO—(CH₂)₂ ence between the two chelates with equal denticity, EDTA and CDTAMA, suggests that the cyclohexyl ring of CDTAMA is providing greater stability to the complex, thereby allowing the $^{111}$In-CDTAMA im- Scheme 2
Synthesis of Cyclohexyl-DTPA and -TTHA

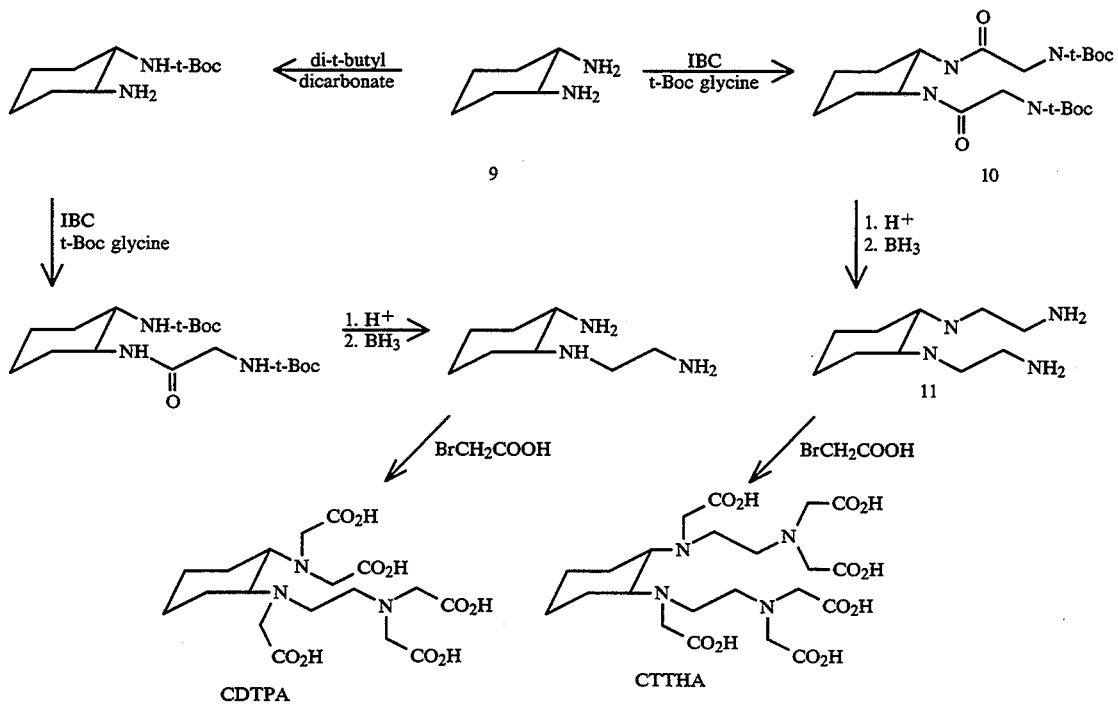

EDTA, CDTAMA and DTPA were conjugated to an anticolon carcinoma antibody, 17-1A, labeled with $^{111}$In, purified by HPLC to remove any crosslinked antibody, diluted with unlabeled 17-1A to provide antibody dose levels of 3 μg, 10 μg, and 25 μg, and injected into normal mice. The biodistribution at 2 hr and 24 hr is given in Table 1. No significant dose effect was observed. CDTAMA immunoconjugates had higher blood and whole body retention and lower kidney uptake than EDTA or DTPA. In fact, the dramatic differmunoconjugate to survive intact longer in the blood. The higher blood and whole body retention as well as the lower uptake in the kidneys of the CDTAMA immunoconjugates compared to these prepared with DTPA suggests that the semi-rigid pentadentate chelate CDTAMA may be providing greater kinetic stability to the metal chelate than the heptadentate non-rigid chelate DTPA.

TABLE 1

Tissue Distribution in Normal Mice of 17-1A Conjugates Labeled with $^{111}$In[a]

| Conjugate | Dose (μg) | Time (hr) | Blood | Liver | Kidney | Bone | Lung | Whole Blood[b] |
|---|---|---|---|---|---|---|---|---|
| EDTA | 3 | 2 | 15.5 | 12.0 | 16.4 | 4.4 | 11.8 | 94 |
|  | 10 | 2 | 18.6 | 12.6 | 16.5 | 4.1 | 12.7 | 98 |
|  | 25 | 2 | 15.6 | 12.0 | 21.0 | 5.2 | 12.2 | 99 |
|  | 3 | 24 | 2.3 | 13.8 | 17.7 | 5.7 | 5.5 | 80 |
|  | 10 | 24 | 2.6 | 10.8 | 17.8 | 6.4 | 5.9 | 78 |
|  | 25 | 24 | 2.9 | 12.5 | 19.1 | 5.9 | 5.4 | 81 |
| CDTA | 3 | 2 | 32.6 | 9.6 | 7.0 | 2.4 | 13.8 | 113 |
|  | 10 | 2 | 29.2 | 8.0 | 6.3 | 2.7 | 15.2 | 101 |
|  | 25 | 2 | 26.7 | 7.0 | 5.8 | 2.8 | 13.0 | 98 |
|  | 3 | 24 | 22.5 | 9.0 | 7.0 | 3.2 | 14.5 | 102 |
|  | 10 | 24 | 21.2 | 8.8 | 6.3 | 2.5 | 9.4 | 94 |
|  | 25 | 24 | 19.2 | 8.3 | 5.9 | 2.7 | 11.5 | 93 |
| DTPA | 3 | 2 | 35.8 | 10.5 | 10.0 | 3.9 | 21.2 | 114 |
|  | 10 | 2 | 33.5 | 9.2 | 8.6 | 3.2 | 16.7 | 99 |
|  | 25 | 2 | 25.8 | 7.2 | 7.5 | 2.7 | 14.0 | 91 |
|  | 3 | 24 | 15.7 | 7.0 | 11.0 | 3.7 | 10.1 | 94 |
|  | 10 | 24 | 13.4 | 6.2 | 9.2 | 3.3 | 14.7 | 84 |
|  | 25 | 24 | 12.6 | 6.1 | 9.7 | 3.3 | 14.5 | 84 |

[a]Data (% dose g$^{-1}$) normalized to 25 g body wt.; purification carried out by HPLC using Zorbax GF-250 column, n = 3
[b]Percent injected dose retained Indium-111-17-1A immunoconjugates prepared from CDTAMA, the mono-N-hydroxysuccinimide ester of CDTA (CDTA-NHS), the dianhydride of DTPA (DTPADA), the di-N-hydroxysuccinimide ester of DTPA (DTPA-2NHS), the N-hydroxysuccinimide ester of CDTPA, CTTHA and TTHA (CDTPA-NHS, CTTHA-NHS, and TTHA-NHS), and a mixture of the mono and dianhydride of EDTA were tested in human colon carcinoma (SW948) xenografted nude mice. The biodistribution and tumor/tissue ratios are given in Tables 2 and 3. The positive effect of the cyclohexyl ring of the chelate on the biodistribution can best be seen in the EDTA and TTHA systems. The tumor uptake of CDTAMA and CTTHA-NHS conjugates was 3–4 times higher than EDTAMA/DA and TTHA-NHS conjugates. They also had slower whole body and blood clearance as well as decreased kidney excretion.

In addition the biodistribution and tumor/tissue ratios of CDTA-17-1A (from CDTAMA) was comparable to DTPA-17-1A (from DTPADA) with the exception that CDTA-17-1A had lower kidney retention resulting in higher tumor to kidney ratios. The same general trends are also seen when comparing CDTA-NHS with DTPA-2NHS with the addition of less bone uptake with CDTA-NHS. The biodistribution of CDTPA-NHS is also comparable to DTPA-2NHS with lower kidney retention.

TABLE 2

Tissue Distribution in Nude Tumor Mice of 17-1A IgG Conjugates Labeled with $^{111}$In[a]

| Chelating Agent | n | Time (hr) | Blood | Liver | Kidney | Bone | Tumor | Whole Blood[b] |
|---|---|---|---|---|---|---|---|---|
| EDTAMA/DA | 2 | 24 | 3.2 | 7.3 | 24.5 | 7.2 | 6.2 | 90 |
|  | 6 | 96 | 0.5 | 7.4 | 12.7 | 4.8 | 2.8 | 60 |
| CDTAMA | 4 | 24 | 4.2 | 9.0 | 4.2 | 6.0 | 14.0 | 98 |
|  | 4 | 96 | 1.0 | 7.5 | 4.3 | 2.5 | 6.0 | 75 |
| DTPADA | 6 | 24 | 5.6 | 8.8 | 8.8 | 5.2 | 11.2 | 96 |
|  | 6 | 96 | 2.6 | 6.5 | 11.6 | 3.6 | 9.8 | 71 |
| CDTA-NHS | 4 | 24 | 6.8 | 7.5 | 4.7 | 2.6 | 12.3 | 85 |
|  | 5 | 96 | 0.26 | 7.7 | 3.7 | 2.1 | 3.0 | 50 |
| DTPA-2NHS | 3 | 24 | 11.6 | 6.8 | 12.0 | 4.6 | 14.1 | 94 |
|  | 3 | 96 | 0.4 | 6.6 | 11.5 | 6.3 | 6.0 | 64 |
| CDTPA-NHS | 3 | 24 | 9.8 | 7.2 | 7.3 | 5.5 | 16.8 | 100 |
|  | 3 | 96 | 0.4 | 8.7 | 5.3 | 7.1 | 5.9 | 68 |
| TTHA-NHS | 3 | 24 | 2.0 | 5.4 | 26.3 | 7.6 | 5.4 | 80 |
|  | 3 | 96 | 0.3 | 6.0 | 14.8 | 6.7 | 2.9 | 61 |
| CTTHA-NHS | 3 | 24 | 6.7 | 5.9 | 13.8 | 6.4 | 11.8 | 78 |
|  | 3 | 96 | 2.9 | 5.6 | 9.4 | 5.1 | 9.5 | 71 |

[a]Data (% dose g$^{-1}$) normalized to 25 g body weight, dose = 25 μg, purification carried out by HPLC using Zorbax GF-250 column
[b]Percent Injected dose retained

TABLE 3

Tumor T/Tissue Ratios of Indium-111 Labeled 17-1A- IgG Conjugates in Nude Tumor Mice

| Chelating Agent | Time (hr) | n | T/Blood | T/Liver | T/Bone | T/Kidney |
|---|---|---|---|---|---|---|
| EDTAMA/DA | 24 | 2 | 1.9 | 0.84 | 0.86 | 0.25 |
|  | 96 | 6 | 5.6 | 0.37 | 0.58 | 0.22 |
| CDTAMA | 24 | 4 | 3.3 | 1.6 | 2.3 | 3.3 |
|  | 96 | 4 | 6.0 | 0.8 | 2.4 | 1.4 |
| DTPADA | 24 | 6 | 2.0 | 1.3 | 2.1 | 1.3 |
|  | 96 | 6 | 3.8 | 1.5 | 2.7 | 0.8 |
| CDTA-NHS | 24 | 4 | 1.8 | 1.6 | 4.7 | 2.6 |
|  | 96 | 5 | 11.5 | 0.4 | 1.4 | 0.8 |
| DTPA-2NHS | 24 | 3 | 1.3 | 2.0 | 3.1 | 1.2 |
|  | 96 | 3 | 15 | 0.9 | 1.0 | 0.5 |
| CDTPA-NHS | 24 | 3 | 1.7 | 2.3 | 3.1 | 2.3 |
|  | 96 | 3 | 15 | 0.7 | 0.8 | 1.1 |
| TTHA-NHS | 24 | 3 | 2.7 | 1.0 | 0.7 | 0.2 |
|  | 96 | 3 | 9.7 | 0.5 | 0.4 | 0.2 |
| CTTHA-NHS | 24 | 3 | 1.8 | 2.0 | 1.8 | 0.85 |
|  | 96 | 3 | 3.3 | 1.7 | 1.9 | 1.0 |

$^{111}$In labeled CDTA-(from CDTAMA) and DTPA- (from CTPADA) anti-carcinoembryonic antigen (anti-CEA) F(ab')$_2$ fragments were also evaluated in human colon carcinoma (SW948) xenografted nude mice. The biodistribution and tumor/tissue ratios are given in Tables 4 and 5 respectively. Compared to the DTPA conjugates, the CDTA-anti-CEA fragments gave higher tumor and lower blood, muscle, kidney, spleen, and bone uptake (Table 4). This results in higher tumor/tissue ratios (Table 5).

The immunoconjugates prepared using the chelates of the present invention may be labeled with other clinically useful radiometals. In addition to $^{111}$In discussed above, these radiometals may include $^{99m}$Tc, $^{47}$Sc, $^{64}$Cu, $^{186}$Re, $^{188}$Re, $^{67}$Cu, $^{153}$Sm, $^{199}$Au, $^{109}$Pd, $^{55}$Co, $^{203}$Pb, and $^{97}$Ru. For example, preliminary distribution studies in normal mice using $^{97}$Ru labeled CDTA-17-1A (from CDTAMA) showed faster clearance from blood with lower liver, kidney, bone and lung uptake than $^{111}$In labeled 17-1A-CDTA (Table 6). Lead-203 labeled CDTA-17-1A IgG conjugates exhibit higher tumor uptake and lower liver retention than DTPA-17-1A (Table 7).

TABLE 4

Tissue Distribution in Nude Tumor Mice of Anti-CEA (Fab')$_2$ Conjugates Labeled with Indium$^{111a}$

| Tissue | DTPA$^b$ 24h | DTPA$^b$ 96h | CDTA$^c$ 24h | CDTA$^c$ 96h |
|---|---|---|---|---|
| Tumor | 10.3 | 7.0 | 17.0 | 10.2 |
| Blood | 4.6 | 0.3 | 1.9 | 0.06 |
| Liver | 9.3 | 6.4 | 8.7 | 6.3 |
| Muscle | 0.9 | 0.4 | 1.0 | 0.3 |
| Kidney | 18.2 | 8.8 | 9.0 | 5.5 |
| Spleen | 3.9 | 4.1 | 2.4 | 2.3 |
| Bone | 1.7 | 1.2 | 1.1 | 0.4 |

$^a$Data (% dose g$^{-1}$) normalized to 25 g body wt; dose = 25 µg; purification carried out by HPLC using Zorbax GF-250 column.
$^b$Conjugated to Anti-CEA via its dianhydride
$^c$Conjugated to Anti-CEA via its monoanhydride

TABLE 5

Tumor (T)/Tissue Ratios of Indium-111 Labeled Anti-CEA (F(ab')$_2$) Conjugates in Nude Tumor Mice

| Tissue | DTPA$^b$ 24h | DTPA$^b$ 96h | CDTA$^c$ 24h | CDTA$^c$ 96h |
|---|---|---|---|---|
| Blood | 2.3 | 24.5 | 8.7 | 224 |
| Liver | 1.1 | 1.1 | 2.0 | 1.65 |
| Kidney | 0.6 | 0.8 | 3.6 | 1.9 |
| Muscle | 12.5 | 17.6 | 35.0 | 39 |
| Spleen | 2.7 | 1.8 | 7.7 | 4.4 |
| Bone | 6.2 | 6.2 | 15.4 | 25.2 |

TABLE 6

Tissue Distribution in Normal Mice of 17-1A (IgG) Conjugates Labeled with Ruthenium-97

| Chelate | n | Time | Blood | Liver | Kidney | Bone | Lung | Whole Body |
|---|---|---|---|---|---|---|---|---|
| CDTA | 3 | 24 | 9.8 | 6.3 | 3.3 | 1.9 | 7.0 | 84 |
|  | 3 | 96 | 4.7 | 5.8 | 2.3 | 1.6 | 3.4 | 66 |

TABLE 7

Tissue Distribution in Nude Tumor Mice of 17-1A (IgG) Conjugates Labeled with $^{203}$Pb$^a$

| Chelate | Time Time(h) | n | Blood | Liver | Kidney | Tumor | Whole Body$^b$ |
|---|---|---|---|---|---|---|---|
| CDTA$^c$ | 24 | 3 | 8.6 | 6.4 | 16.5 | 6.1 | 77 |
|  | 96 | 3 | 1.3 | 2.2 | 6.5 | 1.1 | 48 |
| DTPA$^d$ | 24 | 3 | 3.6 | 5.3 | 18.6 | 1.1 | 61 |
|  | 96 | 3 | 0.9 | 2.7 | 6.3 | 0.4 | 35 |

$^a$Data (% dose g$^{-1}$) normalized to 25 g body weight; dose = 25 g, purification carried out by HPLC using Zorbax GF-250 column
$^b$Percent injected dose retained
$^c$Conjugated to 17-1A via its monoanhydride
$^d$Conjugated to 17-1A via its dianhydride As a model for the possible use of labeled immunoconjugates for PET imaging, the biodistribution of $^{57}$Co labeled EDTA-, CDTA, DTPA-, and CDTPA-17-1A immunoconjugates was determined (see Table 8). In this study the CDTA (from both CDTAMA and CDTA-NHS) and CDTPA-17-1A immunoconjugates were clearly superior in tumor uptake compared to their non-rigid counterparts.

17-1A-CDTA was labeled with $^{67}$Cu- HPLC analysis of the mouse serum incubates revealed that approximately 70% of the activity remained bound to the antibody after three days at 37° C. This represents a substantial improvement in the serum stability of copper-labeled polyaminocarboxylates. Copper labeled DTPA- and p-isothiocyanato-benzyl EDTA immunoconjugates have been reported to be very unstable in human serum, having only 4% and 5% respectively of the activity still bound to the antibody after incubation at 37° for 24 hr [Cole, Nucl. Med. Biol., 13, 363 (1986)].

TABLE 8

Tissue Distribution in Nude Tumor Mice of 17-1A(IgG) Conjugates Labeled with $^{57}$Co$^a$

| Chelating Agent | Time (h) | n | Blood | Liver | Kidney | Tumor | Whole Body$^b$ |
|---|---|---|---|---|---|---|---|
| EDTAMA/DA | 24 | 3 | 22 | 4.1 | 3.0 | 3.1 | 35 |
|  | 96 | 3 | 0.2 | 2.0 | 1.2 | 0.5 | 10 |
| CDTAMA | 24 | 5 | 12.9 | 5.7 | 3.5 | 12.8 | 79 |
|  | 96 | 5 | 1.5 | 2.7 | 1.9 | 4.1 | 31 |
| DTPADA | 24 | 6 | 2.2 | 5.8 | 3.6 | 5.6 | 41 |
|  | 96 | 7 | 0.4 | 2.2 | 1.6 | 0.9 | 10 |
| CDTANHS | 24 | 5 | 6.0 | 7.2 | 3.3 | 14.2 | 78 |
|  | 96 | 4 | 5.5 | 3.2 | 2.5 | 11.2 | 41 |
| DTPA-2NHS | 24 | 3 | 5.2 | 6.1 | 3.8 | 6.2 | 41 |
|  | 96 | 3 | 0.3 | 1.8 | 1.7 | 0.8 | 11 |
| CDTPA-NHS | 24 | 3 | 3.9 | 5.0 | 3.0 | 6.4 | 46 |
|  | 96 | 3 | 1.0 | 1.8 | 1.3 | 2.3 | 15 |

In order to evaluate the effect of various linker/spacer groups on the biodistribution of In-111 labeled antibodies, the CDTA-linker-spacers outlined in Scheme 1 were conjugated to anti-CEA IgG, labeled with $^{111}$In and injected into normal mice. The linkers/spacers included a carbon spacer (CDTAN(CH$_2$)$_2$NCS), a diarylether (CDTANφ-O-φNCS), a dialkylether (CDTAN(CH$_2$)$_2$NHC(O)CH$_2$OCH$_2$CO$_2$NHS), diarylmethylene, (CDTANφCH$_2$φNCS), thioether (CDTAN(CH$_2$)$_2$N-C(O)(CH$_2$)$_2$S(CH$_2$)$_2$CO$_2$NHS, diester (CDTAN(CH$_2$)$_2$NC(O)(CH$_2$)$_2$C(O)OCH$_2$CH$_2$OC-(O)(CH$_2$)$_2$CO$_2$NHS and a disulfide (CDTAN(CH$_2$)$_2$N-C(O)(CH$_2$)$_2$S—S—(CH$_2$)$_2$CO$_2$NHS). The biodistributions in normal mice are given in Table 9 along with that of $^{111}$In labeled Anti-CEA IgG conjugated with CDTAMA and CDTA-NHS as controls. The two-carbon spacer, the dialkylether, and the dialkylthioether each had lower liver retention than the controls (CDTAMA or CDTA-NHS). The diester and disulfide linkage resulted in fast clearance from all tissues. The liver retention of the diester is less than that of the disulfide linkage. The CDTA derivatives with a two carbon spacer and an internal ester were also conjugated to 17-1A IgG, labeled with $^{111}$In and evaluated in mice bearing human xenografted tumors. The biodistribution and tumor/tissue ratios are given in Tables 10 and 11. The CDTA derivatives with two carbon spacer gave higher tumor and lower liver uptake than either CDTAMA or CDTA-NHS (Table 2). This results in higher tumor/liver, tumor/kidney, and tumor/bone ratios compared to CDTAMA and CDTA-NHS (Table 3). The CDTA-diester has lower tumor and non-target tissue uptake with fast whole body clearance. This results in the highest tumor/blood ratio at 24 h. The use of this linker may permit earlier imaging of tumors.

TABLE 9

Tissue Distribution in Normal Mice of $^{111}$In Labeled Anti-CEA (IgG) Conjugates Using CDTA-Linker/spacers[a]

| Chelating Agent | Time(h) | n | Blood | Liver | Kidney | Bone | Whole Body[b] |
|---|---|---|---|---|---|---|---|
| CDTAMA | 24 | 3 | 18.6 | 10.0 | 4.3 | 1.9 | 94 |
|  | 96 | 3 | 10.8 | 9.4 | 3.3 | 1.5 | 65 |
| CDTA-NHS | 24 | 3 | 20.2 | 10.6 | 5.1 | 2.4 | 95 |
|  | 96 | 3 | 12.0 | 10.1 | 3.6 | 1.8 | 73 |
| CDTA-N(CH$_2$)NCS | 24 | 4 | 18.8 | 8.2 | 4.7 | 2.3 | 104 |
|  | 96 | 3 | 11.8 | 7.0 | 3.4 | 1.6 | 75 |
| CDTA-N$\phi$-O-$\phi$-NCS | 24 | 3 | 11.1 | 21.6 | 3.4 | 1.9 | 90 |
|  | 96 | 3 | 2.9 | 18.7 | 1.6 | 0.8 | 44 |
| CDTA-N$\phi$CH$_2\phi$-NCS | 24 | 3 | 9.3 | 25.4 | 2.9 | 1.8 | 88 |
|  | 96 | 3 | 2.3 | 20.4 | 1.2 | 1.0 | 48 |
| CDTAN(CH$_2$)$_2$N-C(O) CH$_2$OCH$_2$CO$_2$NHS | 24 | 3 | 14.9 | 7.7 | 5.2 | 2.1 | 88 |
|  | 96 | 3 | 7.6 | 7.7 | 3.9 | 1.6 | 63 |
| CDTAN(CH$_2$)$_2$NC(O) CH$_2$SCH$_2$CO$_2$NHS | 24 | 3 | 9.6 | 10.6 | 4.0 | 1.6 | 67 |
|  | 96 | 3 | 7.5 | 6.0 | 2.9 | 1.5 | 51 |
| CDTAN(CH$_2$)$_2$NH C(O)(CH$_2$)$_2$C(O)O (CH$_2$)$_2$C(O)(CH$_2$)$_2$ CO$_2$NHS | 24 | 3 | 2.5 | 1.7 | 1.0 | 0.4 | 17 |
|  | 96 | 3 | 1.4 | 1.3 | 0.6 | 0 3 | 11 |
| CDTAN(CH$_2$)$_2$NC(O) (CH$_2$)$_2$S-S-(CH$_2$)$_2$ CO$_2$NHS | 24 | 3 | 1.1 | 3.8 | .9 | 0.4 | 15 |
|  | 96 | 3 | 0.7 | 3.3 | 1.1 | 0.3 | 11 |

TABLE 10

Tissue Distribution in Nude Tumor Mice of 17-1A(IgG) Conjugates Labeled with $^{111}$In Using CDTA-Linker/spacers[a]

| Chelating Agent | Time (h) | n | Blood | Liver | Kidney | Bone | Tumor | Whole Body[b] |
|---|---|---|---|---|---|---|---|---|
| CDTAN(CH$_2$)$_2$NCS | 24 | 5 | 9.8 | 6.4 | 3.0 | 2.8 | 15.2 | 100 |
|  | 96 | 5 | 1.2 | 4.6 | 2.3 | 2.1 | 10.1 | 67 |
| CDTAN(CH$_2$)$_2$NC(O) (CH$_2$)$_2$C(O)O(CH$_2$)$_2$ OC(O)(CH$_2$)$_2$CO$_2$NHS | 6 | 6 | 9.4 | 3.9 | 3.2 | 2.3 | 5.1 | 56 |
|  | 24 | 6 | 1.0 | 2.8 | 1.5 | 1.7 | 4.3 | 31 |
|  | 96 | 6 | 0.3 | 1.2 | 1.0 | 2.1 | 2.3 | 16 |

TABLE 11

Tumor(T)/Tissue Ratios of Indium-111 Labeled 17-1A(IgG) Using CDTA-Linker/spacers[a]

| Chelating Agent | Time(h) | n | T/Blood | T/Liver | T/Bone | T/Kidney |
|---|---|---|---|---|---|---|
| CDTAN(CH$_2$)$_2$NCS | 24 | 5 | 1.6 | 2.4 | 5.4 | 5.1 |
|  | 96 | 5 | 8.5 | 2.2 | 4.8 | 4.5 |
| CDTAN(CH$_2$)$_2$NC(O) (CH$_2$)$_2$C(O)O(CH$_2$)$_2$ OC(O) (CH$_2$)$_2$CO$_2$NHS | 6 | 6 | 0.5 | 1.3 | 2.2 | 1.6 |
|  | 24 | 6 | 4.2 | 1.5 | 2.5 | 2.9 |
|  | 96 | 6 | 6.8 | 1.9 | 4.5 | 2.3 |

The following examples are illustrative of the present invention.

EXAMPLE 1 trans-1,2-diaminocyclohexane N,N,N',N'-tetraacetic acid monoanhydride (CDTAMA)

A mixture consisting of 4.3 g trans-1,2-diaminocyclohexane N, N, N',N'-tetraacetic acid ($1.25 \times 10^{-2}$ moles), 4.0 ml ($5.0 \times 10^{-2}$ moles) pyridine and 9.4 ml ($10.0 \times 10^2$ moles) acetic anhydride was stirred at room temperature for 24 hours. This slurry was filtered and washed extensively with acetic anhydride followed by diethyl ether. The off white solid was collected and dried under vacuum to give 1.7 g (41%) mp 235°–238° C. Concentration of the filtrate yielded an orange sticky solid which was washed with cold methylene chloride to give 1.2 g (31%) of the dianhydride of trans-1,2-diaminocyclohexane N,N,N',N'-tetraacetic acid as an off white solid mp 179°–183° C.

EXAMPLE 2

Synthesis of Triethylenetetramine Hexaacetic Acid Monoanhydride and Mono-N-Hydroxysuccinimide Ester To a suspension of 1.0 g (2.0 mmol) triethylenetetramine hexaacetic acid in 50 ml DMSO was added 1.0 g (5 mmole) dicyclohexylcarbodiimide. This was stirred for 3 days at room temperature until all the granular TTHA crystals were consumed. The fluffy white precipitate of dicyclohexyl urea was filtered and washed with DMSO. The filtrate was split into two equal fractions. The first fraction was concentrated to a thick oil which solidified upon the addition of 30 ml methylene chloride. The solid was collected by filtration, washed with methylene chloride, dried under vacuum to give 0.38 g (80%) of an off white solid mp 100°–115° C. (dec). NMR analysis showed an average of one anhydride/TTHA.

To the second fraction was added 0.92 g (8 mmol) N-hydroxysuccinimide and this was stirred at room temperature for 24 hr then concentrated under reduced pressure to a thick oil. This oil solidified upon the addition of 30 ml methylene chloride. The solid was filtered, wash with cold methylene chloride and dried under reduced pressure to give 0.42 g (71%) of an off white solid. NMR analysis showed an average of one N-hydroxysuccinimide/TTHA mp 124°–140° C.

EXAMPLE 3

Synthesis of Diethylene Triaminepentaacetic Acid Monoanhydride and Mono-N-Hydroxysucciimide Ester To a suspension of 1.0 g (2.5 mmol) diethylenetriamine pentaacetic acid in 50 ml dimethyl sulfoxide (DMSO) was added 1.28 g (6.25 mmol) dicyclohexyl carbodiimide (DCC) and this was stirred for 24 hr at room temperature. During this time the granular solid of DTPA was consumed and the white fluffy solid of dicyclohexyl urea formed. The reaction mixture was filtered and washed with DMSO. The filtrate was split into two equal volumes. The first fraction was concentrated to a thick oil under reduced pressure and heat. A solid precipitated from the oil upon the addition of 30 ml acetonitrile. The solid was collected by filtration, washed with cold acetonitrile and dried under vacuum to give 0.32 g (68%) of a brown solid mp 110°–130° C. NMR analysis revealed an average of one anhydride/DTPA.

To the second fraction was added 1.15 g (10 mmol) N-hydroxysuccinimide. This was stirred at room temperature an additional 24 hr, then concentrated to a thick oil under reduced pressure. Again a solid precipitated from the oil upon the addition of 30 ml acetonitrile. The solid was collected by filtration, washed with cold acetonitrile, and dried under vacuum to give 0.4 g (65%) of a light brown solid. NMR analysis showed an average of one N-hydroxysuccinimide ester/DTPA.

EXAMPLE 4

Synthesis of N,N'-(2-Aminoethyl)-Trans-1,2-Diaminocyclohexane-N,N',N'',N'',N''',N'''Hexaacetic Acid (Cyclohexyl TTHA or CTTHA)

In this example N,N'-(2-aminoethyl)-trans-1,2-diaminocyclohexane-N,N',N'',N''', N''',N'''' hexaactic acid is prepared from the acylation of trans-1,2-diaminocyclohexane with the isobutyl formate of (t-butoxycarbonyl glycine followed by acid hydrolysis of the (t-Boc groups to give N,N'-(glycinamide) trans-1,2-diaminocyclohexane dihydrochloride. Boron hydride reduction gives N,N'-(2-aminoethyl) trans-1,2-diaminocyclohexane tetrahydrochloride which is then alkylated with bromoacetic acid to give CTTHA.

In the first step to a solution consisting of 10.0 g (57.0 mmol) t-butoxycarbonyl glycine, and 5 ml triethylamine dissolved in 300 ml dry THF is added 8.1 ml (62.7 mmol) isobutyl chloroformate. The mixture was allowed to stir at 0° C. for 30 min followed by filtration of the mixture to remove the triethylammonium chloride produced in the reaction. To the filtrate is added 3.4 ml (28.5 mmol) freshly distilled trans 1,2-diaminocyclohexane. The reaction was stirred at 0° C. for 1 hr and then allowed to warm to room temperature and stirred an additional 2 hr. The reaction was then filtered and the filtrate concentrated to a thick oil which solidified upon standing. This solid was recrystallized from ethyl acetate to give 9.5 g (78%) of N,N'-(t-butoxycarbonyl gylcinamide) trans-1,2-diamino cyclohexane as a white solid mp 176°–179° C. In the next step 9.5 g (22.2 mmol) of N,N'-(t-butoxycarbonylgylcinamide) trans-1,2-diamino cyclohexane was stirred overnight with 150 ml acetone and 100 ml 3M HCl. The reaction mixture was then concentrated under reduced pressure to a solid. This solid was washed with methanol, collected and dried to give 4.6 g (70%) of N,N'-(glycinamide) trans 1,2-diaminocyclohexane dihydrochloride as a white solid mp 300°–305° C. (dec).

In the next step 6.6 g (22.0 mmol) of N,N'-(glycinamide) trans-1,2-diaminocyclohexane dihydrochloride was mixed with 300 ml dry THF and cooled to 0° C. under an $N_2$ atmosphere. To this slurry was added 400 ml of 1M $BH_3$-THF. The reaction was allowed to warm to room temperature, then gently refluxed overnight. During this overnight reflux all of the starting material dissolved. The reaction mixture was cooled to 0° C. and quenched by the slow addition of 200 ml of methanol. The solution was concentrated to a thick oil under reduced pressure. This was repeated after the addition of another 100 ml methanol and the addition of 100 ml absolute ethanol. The resulting thick oil was dissolved in 150 ml absolute ethanol, saturated with HCl(g) and refluxed for three hours. During this time a solid formed but upon filtration the solid rapidly absorbed atmospheric moisture. This sticky solid was dissolved in methanol, combined with the ethanol filtrate and concentrated to a thick oil which solidified. This solid was then quickly washed with methanol and dried under vacuum to give 5.5 g (73%) of N,N'-(2-aminoethyl) trans-1,2-diaminocyclohexane tetrahydrochloride as a white solid.

In the last step 4.0 g (11.6 mmol) of N,N'-(2-aminoethyl) trans 1,2-diaminocyclohexane tetrahydrochloride was added to 20 ml water. To this was added 9.7 g bromoacetic acid. The pH was adjusted to pH10 by addition of 7M KOH. The reaction was heated to 45° C. and the pH maintained at pH 10 for 36 hr by the periodic addition of 7M KOH. The reaction was then filtered and the pH adjusted to pH 2.0 by the addition of concentrated HBr. The reaction was then concentrated to a solid under reduced pressure. This solid was dissolved in water and loaded onto an ion-exchange column of AG50W-x8, 200–400 mesh H+ form and washed with 800 ml water followed by 500 ml 2M $NH_4{}^+OH^-$. The product N,N',N'',N''', N''', N'''' hexaacetic acid eluted in the ammonium hydroxide wash. These fractions were collected and concentrated to give 4.5 g (71%) of the product as a glassy white solid.

EXAMPLE 5

Synthesis of N-(2-Aminoethyl)-Trans 1,2-Diaminocyclohexane-N,N',N',N'',N'', Pentaacetic Acid (Cyclohexyl DTPA or CDTPA)

This synthesis starts with the protection of one of the amines of trans 1,2-diaminocyclohexane using di-tert-butyl dicarbonate to give N-(t-butoxycarbonyl) trans-1,2-diaminocyclohexane. The nonprotected amine group is then acylated with the isobutylformate of t-butoxycarbonyl glycine. Both t-Boc group are then hydrolyzed to give N-(glycinamide) trans 1,2-diaminocyclohexane dihydrochloride. Boron hydride reduction of the amide gives N-(2-aminoethyl) trans 1,2-diaminocyclohexane trihydrochloride which is then alkylated with bromoacetic acid to give CDTPA.

In the first step, to a solution consisting of 125 ml (1 mole) trans 1,2-diaminocyclohexane and 400 ml dry THF was added 22 ml (96mmol) di-tertbutyldicarbonate. The reaction was gently refluxed for 3 hr, cooled to room temperature and allowed to stand overnight. The reaction mixture was then filtered and concentrated under reduced pressure. The excess trans 1,2-diaminocyclohexane was recovered by vacuum distillation. The slurry remaining in the distillation flask was dissolved in ethyl acetate and purified by flash chromatography (silica gel, ethyl acetate as eluant), followed by recrystallization from ethyl ether to give 12.0 g (58%) of N-(t-butoxycarbonyl)-trans-1,2-diaminocyclohexane as a white solid mp 88°–91° C.

The nonprotected amine is then acylated as follows. A solution consisting of 11.8 g t-butoxylcarbonyl glycine (67.2 mmol), 9.4 ml triethylamine (67.2 mmol) and 200 ml dry THF was cooled to 0° C. under an $N_2$ atmosphere. To this solution was added 8.7 ml (67.2 mmol) isobutylchloroformate. This mixture was stirred at 0° C. for 30 min. The resulting triethylammonium chloride was removed by filtration and to the filtrate was added N-(t-butoxycarbonyl)-trans 1,2-diaminocyclohexane. The reaction was stirred at 0° C. for 1 hr, allowed to warm to room temperature and stirred for 3 hr. The reaction mixture was then filtered and the filtrate concentrated under reduced pressure to give an orange solid. This solid was recrystallized from a diethyl ether/petroleum ether mixture to give 18.9 g (89%) of N-(t-butoxycarbonyl)-N'(t-butoxycarbonylgylcinamide) trans 1,2-diaminocyclohexane as a white solid mp 163°–166° C.

In the next step the t-Boc protecting groups are removed by acid hydrolysis. A mixture of 15.5 g (41.8 mmol) N-(t-butoxycarbonyl)-N'(t-butoxycarbonylgylcinamide) trans-1,2-diaminocyclohexane, 200 ml acetone, and 225 ml of 3MHCl was stirred overnight at room temperature. The reaction mixture was then concentrated to a solid under reduced pressure. This solid was recrystallized from methanol to give 7.7 g (76%) of N-(glycinamide) trans 1,2-diaminocyclohexane dihydrochloride as a white solid mp 330°–334° C. (dec).

In the next step the amide group is reduced. To a slurry consisting of 1.5 g (6.2 mmol) N-(glycinamide) trans 1,2-diaminocyclohexane dihydrochloride in 150 ml dry THF which was cooled to 0° C. under an $N_2$ atmosphere was added 140 ml of 1M $BH_3$-THF. The reaction was allowed to warm to room temperature, then refluxed for 30 hr. The reaction was then cooled to 0° C. and quenched with 50 ml methanol. The reaction mixture was filtered and the filtrate concentrated to a thick oil under reduced pressure. The oil was dissolved in 100 ml methanol and reconcentrated. This was then repeated with 150 ml absolute ethanol. The oil was then dissolved in 100 ml absolute ethanol and saturated with HCl(g), refluxed for 3 hr, and cooled at 0° C. for 24 hr. A white solid formed and was collected by filtration and washed with cold ethanol to give 0.88 g (54%) of N-(2-aminoethyl) trans-1,2-diaminocyclohexane trihydrochloride as a white solid mp 265°–275° C.

In the last step the amines are alkylated with bromoacetic acid. To a solution consisting of 3.15 g (11.8 mmol) N-(2-aminoethyl) trans 1,2-diaminocyclohexane trihydrochloride and 15 ml water was added 5 ml 7MKOH and 4.0 g (28.8 mmol) bromoacetic acid. The pH was adjusted to pH 10 by addition of 7M KOH. The reaction was heated to 45° C. and the pH maintained at pH 10 for 5 days by the addition of 7M KOH. The reaction was then filtered and the pH adjusted to pH 2 by the addition of concentrated HBr. The reaction was then concentrated to a solid under reduced pressure. This solid was dissolved in water and loaded onto an ion-exchange column of AG50W-X8, 200–400 mesh H+ form and washed with 800 ml water followed by 500 ml 2M ammonium hydroxide. The product eluted in the ammonium hydroxide wash and these fractions were collected and concentrated to give 3.4 g (64%) of N-(2-aminoethyl)-trans-1,2-diaminocyclohexane-N,N',N',N'',N''-pentaacetic acid.

EXAMPLE 6

Synthesis of the di-N-Hydroxysuccinimide Ester of N-(2-Aminoethyl)-Trans-1,2-Diaminocyclohexane-N,N',N',N'',N'',Pentaacetic Acid To a solution consisting of 0.3 g (0.67 mmol) N-(2-aminoethyl) trans-1,2-diaminocyclohexane-N,N',N',N'',N''pentaacetic acid in 20 ml dimethylsulfoxide was added 0.62 g (5.4 mmol) N-hydroxysuccinimide and 0.41 g (2.0 mmol) dicyclohexylcarbodiimide. This was stirred at room temperature for 24 hr. A white fluffy solid of dicyclohexyl urea formed in the reaction and was filtered. The filtrate was concentrated to a thick oil under reduced pressure. A solid precipitated from the oil upon the addition of acetonitrile. This solid was collected, washed with acetonitrile and dried under vacuum to give 0.25 g of the final product. NMR showed an average of 2 NHS esters so the yield is 58%. No further purification was attempted; mp 100°–130° C.

EXAMPLE 7

Synthesis of the Di-N-Hydroxysuccinimide Ester of N,N'-(2-Aminoethyl)-Trans-1,2-Diaminocyclohexane-N,N',N'',N''',N''N'''Hexaacetic Acid To a solution consisting of 0.7 g (1.3 mmol) N,N'-(2-aminoethyl) trans-1,2-diaminocyclohexane-N,N',N'',N''',N''hexaacetic acid in 50 ml dimethylsulfoxide was added 0.9 g (7.8 mmol) N-hydroxysuccinimide and 0.8 g (3.9 mmol) dicyclohexylcarbodiimide. This was stirred at room temperature for 48 hr., during which the white fluffy solid of dicyclohexyl urea formed. This solid was removed by filtration and the filtrate was concentrated to a thick oil under reduced pressure. A solid precipitated from the oil upon the addition of acetonitrile. This solid was collected, washed with cold acetonitrile and dried under vacuum to give 0.54 g of a light brown solid. NMR showed an average of 2 NHS esters so the yield is 56%. No further purification of the solid was attempted; mp 125°–140° C.

EXAMPLE 8

Synthesis of the N-Hydroxysuccinimide Ester of Trans-1,2-Diaminocyclohexane-N,N,N',N'Tetraacetic Acid

Method One

A mixture consisting of 1.0 g trans-1,2-diaminocyclohexane-N,N,N',N' tetraacetic acid (2.9 mmol) in 50 ml dimethyl sulfoxide was heated to 100° C. for 1 hr to dissolve all the CDTA. The solution was then cooled to room temperature and 2.7 g (23 mmol) N-hydroxysuccinimide and 1.2 g (5.8 mmol) dicyclohexyl carbodiimide was added. This was stirred at room temperature for 24 hr during which the white fluffy precipitate of dicyclohexyl urea formed. This solid was filtered and the filtrate was concentrated to a thick oil. A precipitate formed in the oil upon the addition of acetonitrile. This precipitate was collected by vacuum filtration, washed with cold acetonitrile and dried under vacuum to give 0.74 g of a light brown solid mp 135°–142° C. NMR showed an average of one NHS ester; yield is 58%. No further purification was attempted.

Method Two

A mixture consisting of 1.0 g (3.0 mmol) CDTAMA in 50 ml dimethylsulfoxide was heated to 80° C. for 1 hr to dissolve all the CDTAMA then cooled to room temperature. To this was added 3.0 g (26 mmol) N-hydroxysuccinimide. This was stirred at room temperature for 4 hr, then concentrated under reduced pressure to give a thick oil in which a white solid formed upon the addition of 50 ml acetonitrile. The white solid was collected by filtration, washed with cold acetonitrile and dried under vacuum to give 0.52 g (38%) of the product as a white solid; mp 159°–162° C.

EXAMPLE 9

Synthesis of the Isothiocyanate of N-[Methyl(4-4'-methylenedianiline)carbamide]-trans-1,2-diaminocyclohexane-N,N',N'-triacetic acid This synthesis again starts with a monoprotected diamine. To a solution consisting of 8.0 g (40 mmol) 4,4'-methylenedianiline in 60 ml dry chloroform and 0.85 ml triethylamine is added dropwise a solution of 1 g BOC-ON dissolved in 20 ml chloroform. This reaction is allowed to stir at room temperature for 6 days. The reaction mixture is then filtered and the filtrate evaporated to a solid. This solid is then purified by silica gel column chromatography (70% petroleum ether/30% ethyl acetate as eluant) to give 6.7 g (55%) of N-(t-butoxylcarbonyl)-4,4'methylenedianiline.

To a solution of 2.72 g (9 mmol) N-(t-butoxylcarbonyl)-4,4-methylenedianiline dissolved in 100 ml dry DMSO was added in three portions a total of 2.0 g (6 mmol) CDTAMA over a period of 0.5 h. This was stirred overnight, then evaporated to dryness. To the residue was added 200 ml chloroform. The remaining solid was filtered and dried under vacuum to give 3.2 g (86%) of N'-[methyl(N-(t-butoxycarbonyl)-4,4'-methylenedianiline)carbamide)-trans1,2-diamino cyclohexane N', N'', N'' triacetic acid as a white solid.

To a solution of 10 ml 3M HCl and 15 ml acetone was added 0.5 g (0.88 mmol) N'-[methyl (N-(t-butoxycarbonyl)-4,4'-methylenedianiline)carbamide-trans-1,2-diaminocyclohexane N,N'',N''-triacetic acid. This was stirred at room temperature then the acetone was slowly evaporated. To this was added 0.67 ml (8.8 mmol) thiophosgene and 0.2 ml carbon tetrachloride. This was stirred for 12 h extracted with 3×20 ml chloroform. The aqueous layer was concentrated. The residue was washed with H$_2$O, filtered and dried to give the product as 0.32 g (5.90) of a white powder.

EXAMPLE 10

Synthesis of N-[Methyl(2-Aminoethyl)carbamide]Trans-1,2-Diaminocyclohexane N,N',N'-Triacetic Acid To a solution of 4 ml (60 mmol) ethylenediamine dissolved in 30 ml DMSO was added 1 g (3 mmole) CDTAMA. This was stirred at room temperature under a nitrogen atmosphere overnight. The DMSO was evaporated under reduced pressure. The residue was recrystalized from absolute ethyl alcohol to give 0.75 g (64%) of a white solid mp 177°–179° C.

EXAMPLE 11

Synthesis of Dilithium Salt of N-[methyl(2-Isothiocyanatoethyl) Carbamide]Trans-1,2-Diaminocyclohexane N,N',N-Triacetic Acid To a solution of 20 ml 1/1 methanol/water was added 1.0 g (2.6 mmole) N-[methyl(2-aminoethyl)carbamide]-trans-1,2-diaminocyclohexane N,N',N'-triacetic acid. To this was added 0.32 g (7.7 mmole) lithium hydroxide monohydrate. This was stirred at room temperature 1 hr then concentrated to a yellow solid. The solid was dissolved in 3 ml methanol and precipitated with excess acetone to give 0.8 g of a white solid. This solid was dissolved in 20 ml methanol and 10.8 ml of a 0.2M solution of thiophosgene in methylene chloride was added followed by stirring at room temperature for 2 h. The solvent was evaporated and the residue dissolved in 2 ml methanol. The product 0.56 g (63%) was precipitated by the addition of 50 ml acetone.

EXAMPLE 12

Synthesis of N-[methyl(2-bromoacetamidoethyl) carbamide]-trans-1,2-diaminocyclohexane N,N',N'-triacetic acid Attempts to prepare this compound with excess bromoacetyl bromide under aqueous conditions using the procedure of DeRiemer, et al. (*J. Med. Chem.*, 22:1019, 1979; *J. Labelled Compd. Radiopharm.*, 18:1517 (1981)) failed. This synthesis required a mild acylation reaction under nonaqueous conditions. For this purpose a new activated ester N-hydroxysuccinimidyl-bromoacetate was prepared as follows. Into 150 ml of dry methylene chloride was placed 20.0 g -bromoacetic acid (0.143 mol), 18.1 g N-hydroxysuccinimide (0.157 mol) and 32.4 g dicyclohexylcarbadiimide (0.157 mol). This was stirred overnight under a nitrogen atmosphere. The by-product, dicyclohexylurea was filtered off and the filtrate concentrated under reduced pressure to a solid. The solid was recrystalized from an ethyl acetate/ethyl ether mixture to give 22 g (65%) of a white solid mp 111°–113° C. Next, 0.5 g (1.28 mmol) of N-[methyl(2-aminoethyl)carbamide]-trans-1,2-diaminocyclohexane N,N',N'-triacetic acid was added in small portions over a period of 2 hr to a solution consisting of 3.0 g (12.8 mmol) N-hydroxysuccinimidyl-bromoacetate dissolved in 30 ml dry DMSO. After the addition was complete the reaction was stirred overnight under a nitrogen atmosphere, then concentrated under reduced pressure. The residue was dissolved in 5 ml absolute ethanol and the product precipitated by the addition of 250 ml acetone. The precipitate was collected by filtration, washed with excess acetone and dried under vacuum to give 0.47 g (72%) of a light yellow solid mp 120° C. dec.

EXAMPLE 13

Synthesis of N-[methyl -(2-amidoethyl-ethylenegylcol succinimidylsuccinate]-trans-1,2-diaminocyclohexane-N,N',N'triacetic acid A solution consisting of 10 g ethyleneglycol-bis succinic acid (38 mmole) and 9.65 g (84 mmole) N-hydroxysuccinimide dissolved in 200 ml acetonitrile was cooled to 0°–2° C. To this was added 19.5 g (95 mmole) dicyclohexylcarbodiimide. This was allowed to warm to room temperature, stirred overnight, then filtered.

The filtrate was concentrated to a thick oil which solidified upon standing. The solid was recrystalized from chloroform to give 13.1 g (75%) of a white solid mp 129°–130° C. 11.7 g (26 mmol) of the white solid was then added to 100 ml dry DMSO (stored over 4A molecular sieves). To this was added in small portions a total of 1.0 g (2.6 mmole) of N-[methyl(2-aminoethyl)-carbamide]-trans-1,2-diaminocyclohexane-N,N',N'-triacetic acid over a period of eight hours. This mixture was stirred an additional 12 hours, then concentrated to a thick oil. The product precipitated upon the addition of 500 ml methylene chloride to give 0.96 g (51%) of a white powder.

EXAMPLE 14

Antibody Conjugation Using The Anhydrides

In this example CDTA is attached to the anticolon Ca 17-1A antibody using either its mono- or dianhydride and the extent of crosslinking is determined by gel filtration HPLC. To the 17-1A antibody in 0.1 N sodium bicarbonate at an antibody concentration of 20 mg/ml was added CDTAMA in DMSO at a molar ratio of CDTAMA/antibody of 10/1 or CDTADA in a molar ratio of 5/1. These solutions were allowed to incubate at 4° C. overnight. The uncoupled CDTA was removed using a Centricon C-30 centrifugation/filtration device. The average number of chelates per antibody was determined by the radiocobalt assay of Meares, et al. [Anal. Biochem 142, 68 (1984)] to be 3 CDTA/antibody. Solutions, containing either 200 mg unmodified 17-1A, 200 mg CDTADA conjugated 17-1A, or 200 mg CDTAMA conjugated 17-1A were assayed by HPLC on a Zorbax GF-250 column with 0.2M phosphate buffer, pH 7.0, flow rate 1.0 ml/min. Chromatography showed extensive crosslinking for the CDTADA conjugated 17-1A while the CDTAMA conjugated 17-1A was indistinguishable from unmodified 17-1A.

EXAMPLE 15

Example of Antibody Conjugation Using N-hydroxysuccinimide Esters

In this example the mono-N-hydroxysuccinimide of CDTA, prepared by Method 1, and the di-N-hydroxysuccinimide ester of DTPA prepared by the method of Najafi [Najafi, et al., Appl. Radiat. Isol., 37, 548 (1986)] was used to prepare 17-1A immunoconjugates. To the 17-1A antibody in a 0.1M phosphate buffer pH 7.0 at an antibody concentration of 20 mg/ml was added CDTA-1NHS in DMSO at a molar ratio of CDTA-1NHS to antibody of 10/1, and either DTPA-2NHS at a molar ratio to antibody of 10/1. These solutions were allowed to incubate at 4° C. overnight. The uncoupled chelates were removed and the buffer changed to 0.1N NaHCO$_3$ using a Centricon C-30 centrifugation filtration device. The average number of chelates per antibody was determined by the radiocobalt assay of Meares to be 3 CDTA/antibody and 3 DTPA/antibody. Assays of each preparation on HPLC (Zorbax GF-250 column) showed no crosslinking using CDTA-1NHS and approximately 5% crosslinking with DTPA-2NHS.

EXAMPLE 16

$^{111}$In-17-1A Immunoconjugate Biodistribution

In this example the biodistribution of the $^{111}$In-17-1A immunoconjugates are compared. CDTA was conjugated to 17-1A using CDTAMA as described in an earlier example. DTPA was conjugated using its dianhydride using the procedure of Hnatowich, et al., J. Immunol. Meth. 65, 147 (1983) and using its di-N-hydroxysuccinimide ester using the procedure of Najafi, et al., Appl. Radiat. Isol., 37, 548 (1986). CDTPA and CTTHA were conjugated using their di-N-hydroxysuccinimide esters as described in an earlier example. TTHA was conjugated using its mono-N-hydroxysuccinimide ester prepared analogously to CTTHA. EDTA was conjugated using a mixture of its mono and dianhydride which was prepared by a room temperature dehydration reaction using pyridine and acetic anhydride. The average number of chelates per antibody was determined by the radiocobalt assay of Meares, et al. to be 3, 3, 3, 1, 2 and 1 for EDTA, CDTA, DTPA, CDTPA, TTHA and CTTHA respectively. The immunoconjugates were labeled with $^{111}$In in an acetate (0.1M)/citrate (0.02M) buffer, pH5 and purified by HPLC on a Zorbax GF-250 column using 0.2M, pH7 phosphate buffer and only the monomeric fractions were collected and utilized in the biodistribution studies. This was done to make an equal comparison of the chelates by eliminating the effects of antibody crosslinking. The labeled immunoconjugates were then injected intravenously (tall vein) into human colon ca (SW948) xenografted nude mice and the mice then sacrificed at 24 and 96 hrs. The distribution is as shown in Table 2 above.

EXAMPLE 17

$^{57}$Co-Immunoconjugate Biodistribution

In this example the biodistribution of the $^{57}$Co-17-1A immunoconjugates is compared. CDTA was conjugated using both its monoanhydride and its mono N-hydroxysuccinimide ester as described in an earlier example. DTPA was conjugated using its dianhydride using the procedure of Hnatowich, et al., J. Immunol. Meth., 65, 147 (1983). CDTPA was conjugated as described earlier using its 2NHS ester. The average number of chelates/antibody was determined by the radiocobalt assay of Meares, et al., to be 3, 3, 3, 3 and 1 for EDTA, CDTA (from CDTAMA), CDTA (from CDTA-1NHS), DTPA (from DTPADA), DTPA (from DTPA-2NHS), and CDTPA respectively. The immunoconjugates were labeled with $^{57}$Co in a 0.02M citrate buffer and purified by HPLC on a Zorbax GF-250 column using 0.2M, pH7, phosphate buffer. Only the monomeric fractions were collected and utilized in the biodistribution studies. The labeled immunoconjugates were then injected intravenously (tail vein) into human colon ca (SW948) xenografted nude mice and the mice then sacrificed at 24 and 96 hrs. The distribution is as shown in Table 8 above.

EXAMPLE 18

$^{111}$In-Anti-CEA F(ab')$_2$—Immunoconjugate Biodistribution

In this example the biodistribution of $^{111}$In-CDTA-antiCEA and $^{111}$In-DTPA-antiCEA F(ab')$_2$ fragments were compared. CDTA and DTPA were conjugated to anti-CEA F(ab')$_2$ using CDTAMA and DTPADA respectively as described earlier. The average number of chelates per antibody was determined by the radiocobalt assay of Meares, et al. to be 3 and 2 for CDTA and DTPA respectively. The preparations were labeled with $^{111}$In and purified by HPLC as described in an earlier example. The labeled-anti-CEA was injected intravenously (tall vein) in human colon ca (SW948)

xenografted nude mice and the mice sacrificed at 24 and 96 h. The distribution is as shown in Tables 4 and 5.

EXAMPLE 19

$^{97}$Ru-Immunoconjugate Biodistribution

In this example the biodistribution of $^{97}$Ru-CDTA-17-1A is evaluated. CDTA was conjugated to 17-1A using CDTAMA as described in an earlier example. The average number of chelates per antibody was determined by the radiocobalt assay of Meares, et al. to be 3. 17-1A-CDTA was labeled with $^{97}$Ru in a 0.1M citrate buffer pH5, by incubation with either stannous citrate or stannous DTPA as a reducing agent overnight at 37° C., followed by purification by HPLC on a Zorbax GF-250 column using 0.2M, pH7 phosphate buffer. The labeled-17-1A was injected intravenously (tail vein) into human colon ca (SW948) xenografted nude mice and the mice sacrificed at 24 and 96 h. The distribution is as shown In Table 6 above.

EXAMPLE 20

$^{203}$Pb-Immunoconjugate Biodistribution

In this example the biodistribution of the $^{203}$Pb-17-1A immunoconjugates are compared. CDTA and DTPA were conjugated to 17-1A using CDTAMA and DTPADA respectively as described earlier. The average number of chelate per antibody was determined by the radiocobalt assay of Meares, et al. to 3 for both preparations. The conjugates were labeled with $^{203}$Pb at pH8 in the presence of 0.02M citrate/0.1M NaHCO$_3$ overnight at 37° C. The preparations were challenged with 10mM EDTA and purified by HPLC on a Zorbax GF-250 column using 0.2M, pH7 phosphate buffer as eluate. The monomer fractions were collected and utilized in the biodistribution studies. The labeled-17-1A conjugates were injected intravenously (tail vein) into human colon ca (SW948) xenografted nude mice and the mice sacrificed at 24 and 96 h. The distribution is as shown in Table 7 above.

EXAMPLE 21

Conjugation with Isothiocyanates and Bromoaceticamides

In this example N-[methyl(2-aminoethyl)carbamide]-trans-1,2-diaminocyclohexane N,N',N'-triacetic acid was conjugated to the anticolon ca 17-1A antibody using either its isothiocyanato or its bromoacetamido- derivative. To the 17-1A antibody in 0.1 N sodium bicarbonate (pH 8) at an antibody concentration of 20 mg/ml was added the dilithium salt of N-[methyl(2-isothiocyanatoethylcarbamide] trans-1,2-diaminocyclohexane-N,N',N'-triacetic acid in DMSO at a molar ratio of 20/1. Also to a different sample of 17-1A in 0.1N sodium bicarbonate (pH 8) at an antibody concentration of 10 mg/ml was added N-[methyl(2-bromoacetamidoethyl)carbamide]-trans-1,2-diamino cyclohexane N,N',N'-triacetic acid in DMSO at a molar ratio of 20/1. These solutions were allowed to incubate at 37° C. overnight. The uncoupled chelate was removed using a Centricon C-30 centrifugation/filtration device. The average number of chelates per antibody was determined by the radiocobalt assay of Meares, et al. [*Anal. Biochem.*, 142, 68 (1984)] to be 2 and 1.5 for the isothiocyanate and bromoacetamide respectively.

EXAMPLE 22

Biodistribution of $^{111}$In Labeled CDTA-Linker/Spacer AntiCEA(IgG) Immunoconjugates in Normal Mice In this example the biodistribution of $^{111}$N-AntiCEA-CDTA Linker/Spacer immunoconjugates are compared to CDTA-AntiCEA immunoconjugates. CDTA was conjugated to AntiCEA IgG using CDTAMA and CDTA-NHS as described earlier. The isothiocyanates, CDTA-N(CH$_2$)$_2$NCS, CDTA-N$\phi$-O-$\phi$-NCS, and CDTAN$\phi$CH$_2\phi$NCS were conjugated as described earlier using a 10 fold molar excess of ligand over antibody. The N-hydroxysuccinimide esters, CDTA-N(CH$_2$)NC(O)CH$_2$OCH$_2$CO$_2$NHS, CDTA-N(CH$_2$)$_2$NC(O)CH$_2$SCH$_2$CO$_2$NHS, CDTA-N(CH$_2$)$_2$NC(O)(CH$_2$)$_2$S—S(CH$_2$)$_2$CO$_2$NHS, and CDTA-N(CH$_2$)$_2$NC(O)(CH$_2$)$_2$C(O)O(CH$_2$)$_2$OC-(O)(CH$_2$)$_2$CO$_2$NHS were conjugated as described for CDTANHS. The immunoconjugates were labeled with $^{111}$In in an acetate (0.1M)/citrate (0.02M) buffer, pH5 and purified by HPLC on a Zorbax GF-250 column using 0.2M, pH 7 phosphate buffer. No crosslinking was observed for CDTAMA, CDTA-NHS, CDTAN(CH$_2$)NCS or the other isothiocyanates. Less than 3% crosslinking was observed for the other NHS esters. Only the monomeric fractions were collected and utilized in the biodistribution studies. The labeled immunoconjugates were then injected intravenously (tail vein) into normal mice and the mice were sacrificed at 24 and 96 hrs. The distribution is shown in Table 9.

EXAMPLE 23

| Mouse Serum Stability Studies of Radiolabeled 17-1A Immunoconjugates | | | |
|---|---|---|---|
| Conjugate | Radiometal | Time, Hr | % Radiometal Remaining With the Antibody |
| DTPA | $^{57}$Co | 24 | 56 |
| CDTA | $^{57}$Co | 24 | 96 |
| trans-CDTPA | $^{57}$Co | 24 | 63 |
| trans-CTTHA | $^{57}$Co | 24 | 50 |
| DTPA | $^{57}$Co | 96 | 28 |
| CDTA | $^{57}$Co | 96 | 41 |
| trans-CDTPA | $^{57}$Co | 96 | 32 |
| trans-CTTHA | $^{57}$Co | 96 | 26 |
| DTPA | $^{203}$Pb | 24 | 5 |
| CDTA | $^{203}$Pb | 24 | 30–50 |
| CDTA | $^{97}$Ru | 96 | 100 |
| CDTA | $^{67}$Cu | 72 | 63 |

17-1A immunoconjugates were prepared as in earlier examples and labeled with $^{57}$Co, $^{203}$Pb, $^{97}$Ru, and $^{67}$Cu. These labeled immunoconjugates were incubated in mouse serum at 37° C. for up to 96 hours. Aliquots were removed and injected onto a Zorbax GF-250 column and 0.2 ml fractions collected. The percent of the injected activity that eluted with the antibody is given in the above table. When labeled with $^{57}$Co and $^{203}$Pb the CDTA immunoconjugates were the most stable. The stability of $^{67}$Cu-CDTA-17-1A is substantially greater than that of a $^{67}$Cu-DTPA immunoconjugate which was reported to have only 4–5% of the activity remaining with the antibody after 24 hrs.

We claim:

1. N-[methyl-(2-amidoethyl-ethyleneglycol succinimidylsuccinate]-trans-1,2-diaminocylo-hexane-N,N',N'-triacetic acid.

2. A compound of the formula

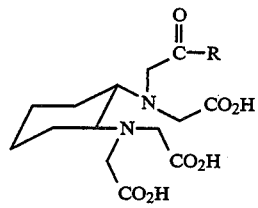

wherein R is selected from the group consisting of

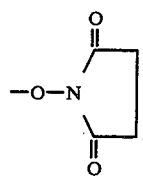

—NHNH$_2$;  and

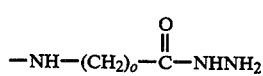

and o is 1 to 6.

3. A compound of the formula

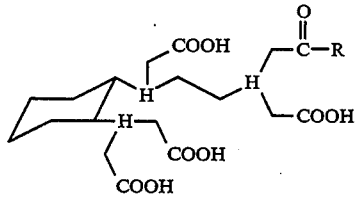

wherein R is selected from the group consisting of

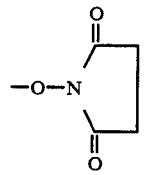

—NHNH$_2$;  and

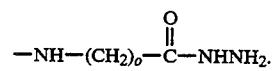

and o is 1 to 6.

4. A compound of the formula

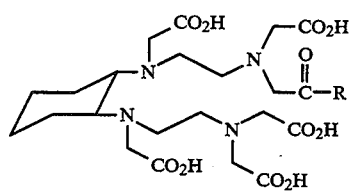

wherein R is selected from the group consisting of

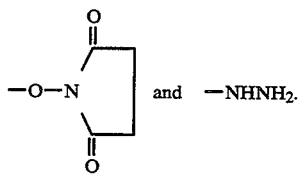 and —NHNH$_2$.

* * * * *